(12) United States Patent
Walker et al.

(10) Patent No.: US 10,145,755 B2
(45) Date of Patent: Dec. 4, 2018

(54) CHARACTERIZATION AND MEASUREMENT OF STORAGE CAVERNS USING MULTIBEAM ULTRASOUND

(71) Applicant: SONASEARCH, INC., Redmond, WA (US)

(72) Inventors: Stephen Edward Walker, Redmond, WA (US); Sheldon Rubin, Redmond, WA (US)

(73) Assignee: Sonasearch, Inc., Waco, TX (US)

( * ) Notice: Subject to any disclaimer, the term of this patent is extended or adjusted under 35 U.S.C. 154(b) by 0 days.

(21) Appl. No.: 14/984,495

(22) Filed: Dec. 30, 2015

(65) Prior Publication Data

US 2017/0191965 A1   Jul. 6, 2017

(51) Int. Cl.
| | | |
|---|---|---|
| *G01S 15/89* | (2006.01) | |
| *G01M 3/24* | (2006.01) | |
| *G01N 29/04* | (2006.01) | |
| *G01N 29/06* | (2006.01) | |
| *G01N 29/26* | (2006.01) | |
| *G01N 29/265* | (2006.01) | |
| *E21B 47/14* | (2006.01) | |
| *G01B 21/18* | (2006.01) | |
| *G01N 29/07* | (2006.01) | |
| *G01N 29/22* | (2006.01) | |

(52) U.S. Cl.
CPC .............. *G01M 3/24* (2013.01); *E21B 47/14* (2013.01); *G01B 21/18* (2013.01); *G01N 29/043* (2013.01); *G01N 29/0618* (2013.01); *G01N 29/07* (2013.01); *G01N 29/225* (2013.01); *G01N 29/262* (2013.01); *G01N 29/265* (2013.01); *G01N 2291/0258* (2013.01); *G01N 2291/0289* (2013.01); *G01N 2291/02854* (2013.01); *G01N 2291/106* (2013.01)

(58) Field of Classification Search
CPC ............. G01S 15/8915; G01S 15/8918; G01S 15/892; G01S 15/8936; G01S 15/8938
USPC .. 367/7, 30, 31, 81, 88, 103, 104, 140, 153, 367/154, 173; 340/856.4
See application file for complete search history.

(56) References Cited

U.S. PATENT DOCUMENTS

| | | | | |
|---|---|---|---|---|
| 5,386,831 A * | 2/1995 | Gluck | ...................... | A61B 5/01 600/474 |
| 5,953,287 A * | 9/1999 | Willacy | .................. | G01S 15/88 367/104 |
| 2006/0114748 A1* | 6/2006 | Rogers | .................... | G01S 15/89 367/88 |
| 2008/0013404 A1* | 1/2008 | Acker | ..................... | G01S 7/003 367/88 |

* cited by examiner

*Primary Examiner* — Kevin Kim
(74) *Attorney, Agent, or Firm* — Cloutier Ortega PLLC (57) ABSTRACT

An objective of this invention is to provide an apparatus and method to more accurately determine the parameters of a storage cavern before and during use, including fluid filled storage caverns. Another object of this invention is to provide a granular inspection of the storage cavern. Another object of this invention is to provide precision positioning information of sample points.

6 Claims, 9 Drawing Sheets

CHARACTERIZATION AND MEASUREMENT OF STORAGE CAVERNS USING MULTIBEAM ULTRASOUND

CROSS-REFERENCES TO RELATED APPLICATIONS

This application takes priority to U.S. patent application Ser. No. 14/924,567, filed on Oct. 27, 2015, which takes priority to U.S. provisional application 62/122,911 filed on Nov. 3, 2014. Each of the above named applications are incorporated herein, in its entirety, by reference.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND

Underground storage caverns have been used for storage since the beginning of time. As early as 1940 underground storage caverns have been used to store natural gas, compressed air, hydrogen, and liquid hydrocarbons (including crude oil), amongst others. In many applications salt caverns have been man-made to hold hydrocarbons. The parameters of a storage caverns must be determined prior to use and during its lifetime since storage caverns decay and/or change shape over time.

Cavern survey logging refers to measurements of storage caverns using acoustic techniques to evaluate the storage cavern size, shape, volume, integrity and other parameters. The survey report is usually presented with the basic measurements and an estimate of cavern parameter change since the previous survey. Survey logging of fluid-filled storage caverns is time-consuming and subject to error from missing storage cavern anomalies and features difficult to characterize.

Figure 1A:
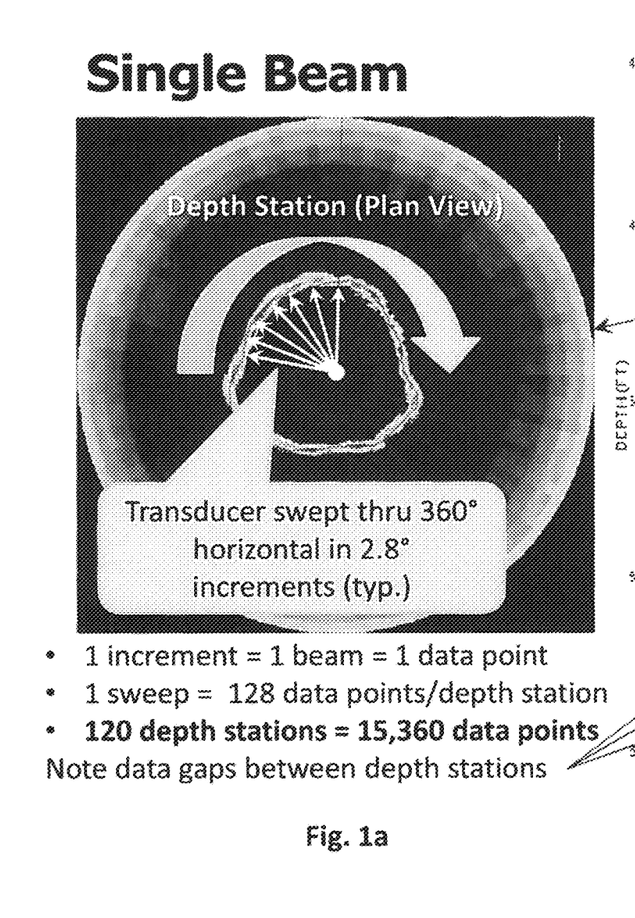
FIG. 1A is a plan view of a prior art cavern logging survey.
Figure 1B:
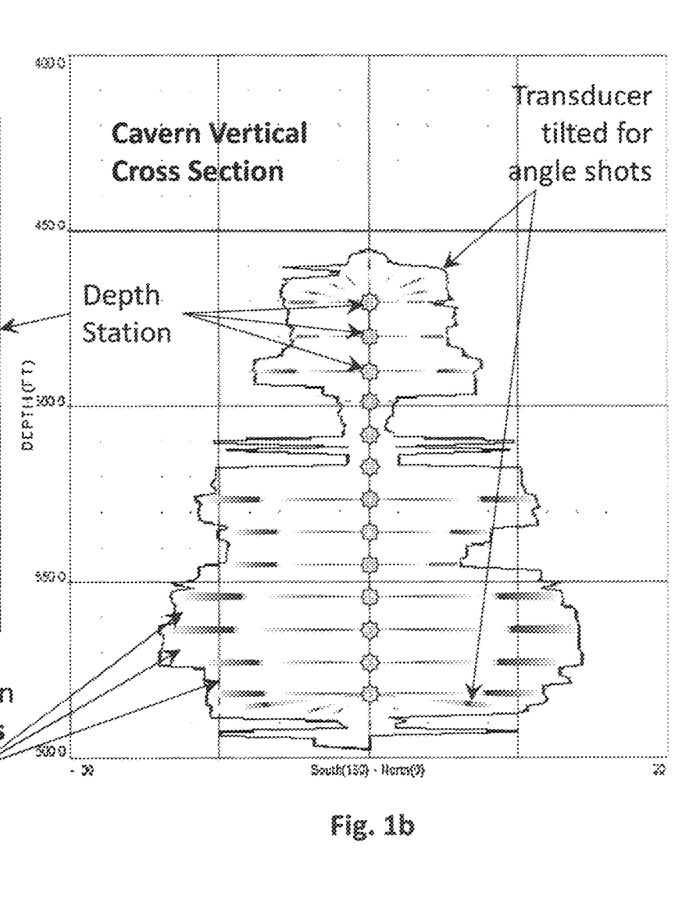
FIG. 1B is a cross-section view of a prior art cavern logging survey.
Figure 2:
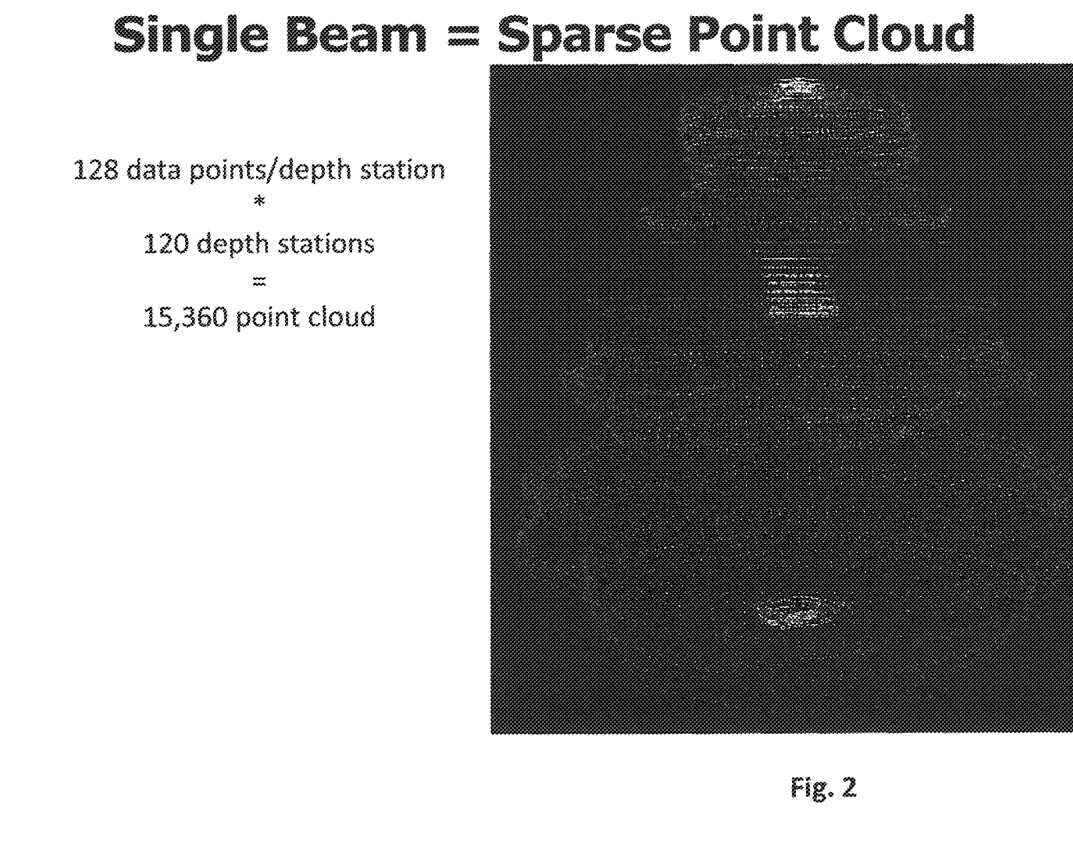
FIG. 2 is a representation of a prior art cavern logging survey.

Current techniques used to measure cavern parameters are lacking. Referring to FIGS. 1a and 1b, in a prior art acoustic technique of measuring storage caverns, a single beam transducer is swept horizontally over 360 degrees at various depths or depth stations. The limited number and type of data points gathered in this technique leave significant information about the storage cavern unknown. Small target detection is difficult, if not impossible, to obtain even with readings at a plurality of depth stations. Prior art techniques are also time consuming and costly. FIG. 2 is a representation of the data obtained from a prior art cavern measuring system. Consequently, there is a need for the reliable, accurate measurement apparatus and method to determine whether and to what extent a storage cavern has undergone a change of shape, remains serviceable or requires remedial action.

SUMMARY OF THE INVENTION

An objective of this invention is to provide an apparatus and method to more accurately determine the parameters of a storage cavern before and during use, including fluid filled storage caverns. Another object of this invention is to provide a granular inspection of the storage cavern. Another object of this invention is to provide precision positioning information of sample points.

BRIEF DESCRIPTION OF THE DRAWINGS

Other features and advantages of the present invention will become apparent in the following detailed descriptions of the preferred embodiment with reference to the accompanying drawings, of which.

DETAILED DESCRIPTION OF THE INVENTION

In the following detailed description, reference is made to the accompanying drawings, which form a part hereof. In the drawings, the use of similar or the same symbols in different drawings typically indicates similar or identical items, unless context dictates otherwise.

The illustrative embodiments described in the detailed description, drawings, and claims are not meant to be limiting. Other embodiments may be utilized, and other changes may be made, without departing from the spirit or scope of the subject matter presented here.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken as limiting.

The present application may use formal outline headings for clarity of presentation. However, it is to be understood that the outline headings are for presentation purposes, and that different types of subject matter may be discussed throughout the application (e.g., device(s)/structure(s) may be described under process(es)/operations heading(s) and/or process(es)/operations may be discussed under structure(s)/process(es) headings; and/or descriptions of single topics may span two or more topic headings). Hence, the use of the formal outline headings is not intended to be in any way limiting.

Figure 8:
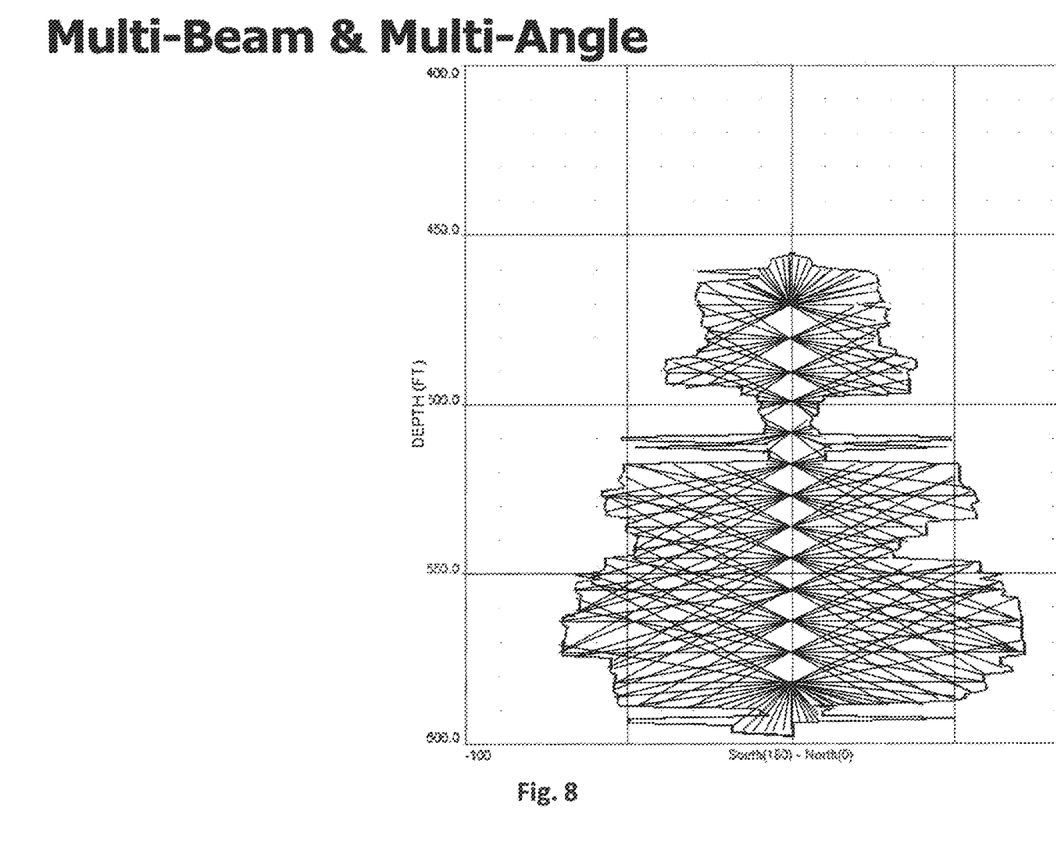
FIG. 8 is a representation of an exemplary cavern logging survey.

Provided herein are embodiments for a cavern surveyor system 100 and methods for use. Referring to FIG. 8, the cavern survey system 100 increases the chances of detecting small/irregular anomalies. Additionally, data maybe collected at fewer depth stations.

Figure 3:
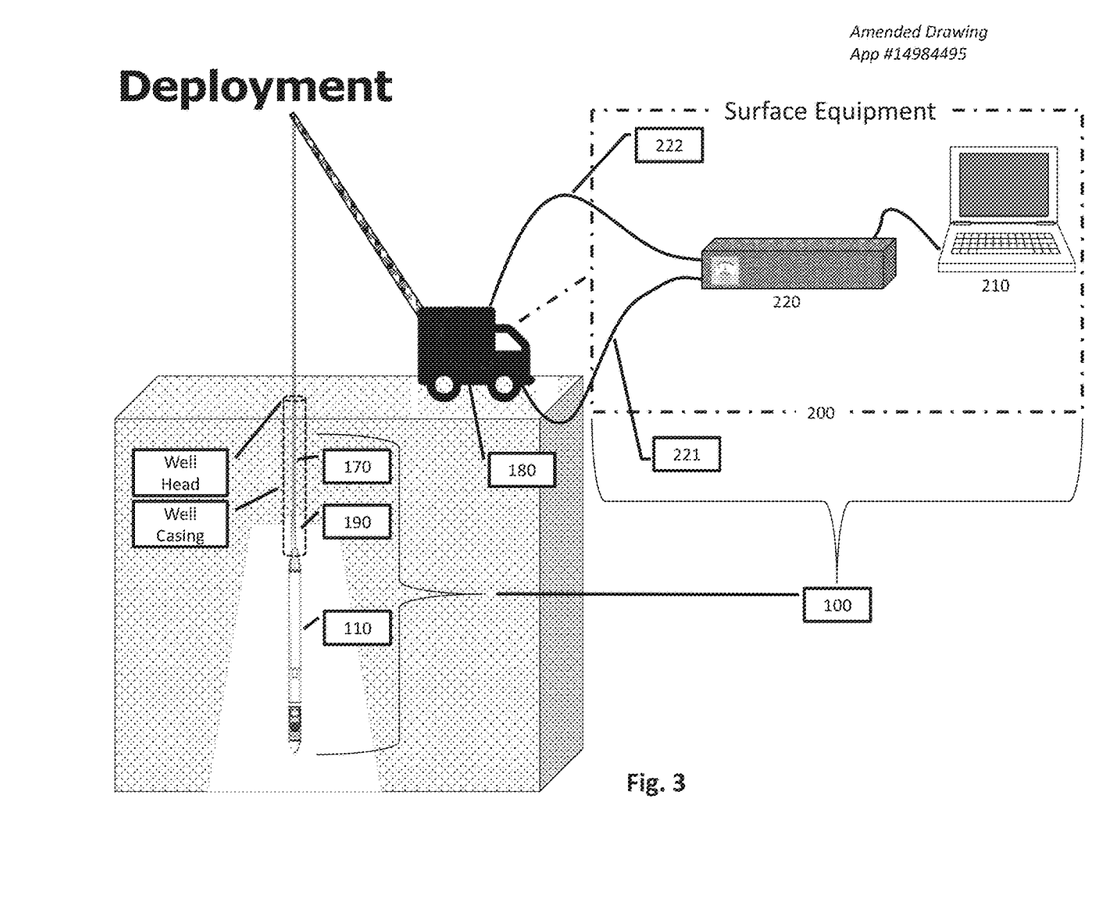
FIG. 3 is a schematic of an embodiment of the cavern survey system.
Figure 4:
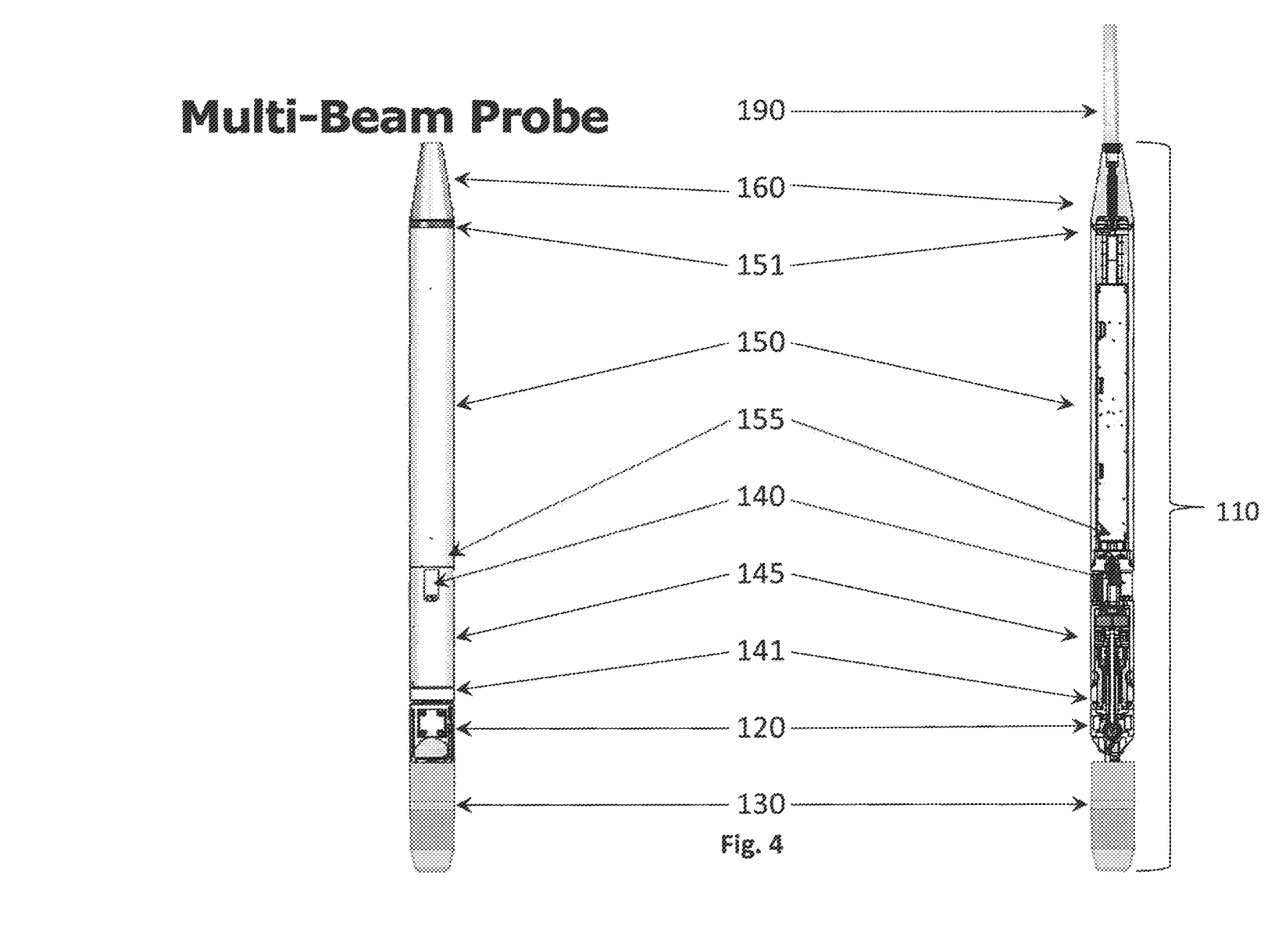
FIG. 4 is a perspective view of an embodiment of the cavern probe.

Referring to FIGS. 3 and 4, the cavern surveyor system 100 is comprised of at least one cavern probe 110 and a telemetry system 200. The cavern probe 110 is comprised of at least one probe transducer 130 and a pan and tilt assembly 120 that receives and transmits data from the telemetry system 200.

Figure 5:
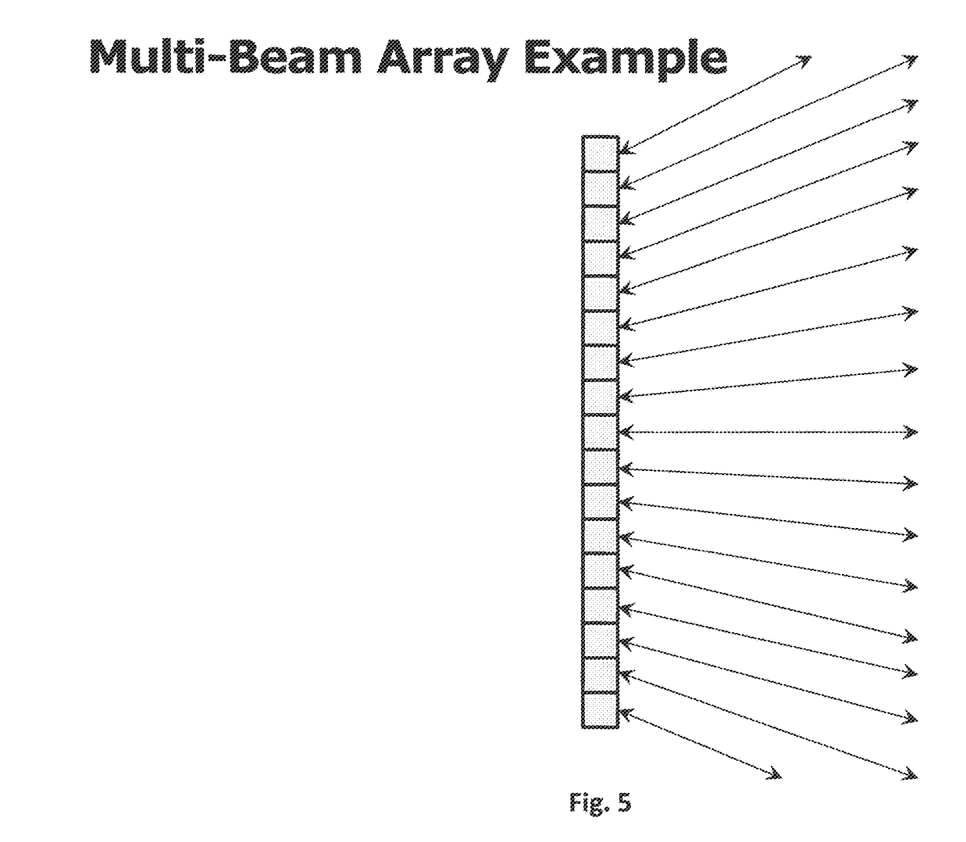
FIG. 5 is a schematic view of an exemplary multi-beam array.

Referring to FIG. 5, preferably, the probe transducer 130 is comprised of a plurality of transducers where the transducers are aligned for directional signal transmission for beamforming or spatial filtering of signals. Beamforming or spatial filtering is a signal processing technique used in sensor arrays for directional signal transmission or reception. This is achieved by combining elements in a phased array in such a way that signals at particular angles experience constructive interference while others experience destructive interference. Beamforming can be used at both the transmitting and receiving ends in order to achieve spatial selectivity. Beamforming can be used for radio or sound waves. Preferably, the beam profile has less than 2 dB drop between transducers allowing a very high density of sample points.

In one embodiment the probe transducer 130 is a multi-beam array having at least 256 equally spaced transducers, where each transducer is vertically orientated to the others, allowing data collection at 45 degrees, from the vertical plane, and 1 degree, from the horizontal plane. In another embodiment, there are 512 probe transducers 130 resulting in an acoustic pattern of 1°×90°.

Figure 6A:
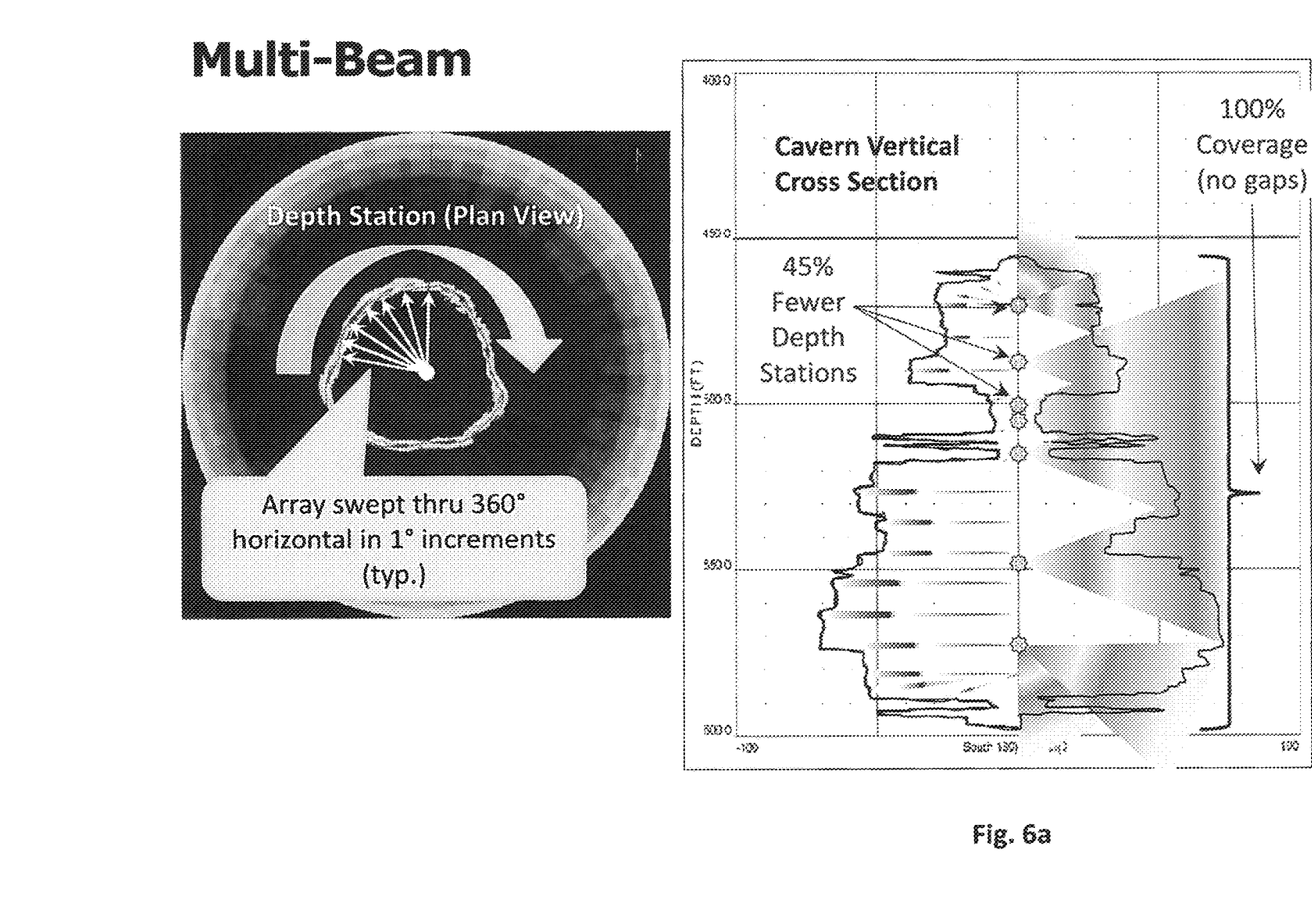
FIG. 6A is a cross sectional view of an exemplary cavern logging survey.
Figure 6B:
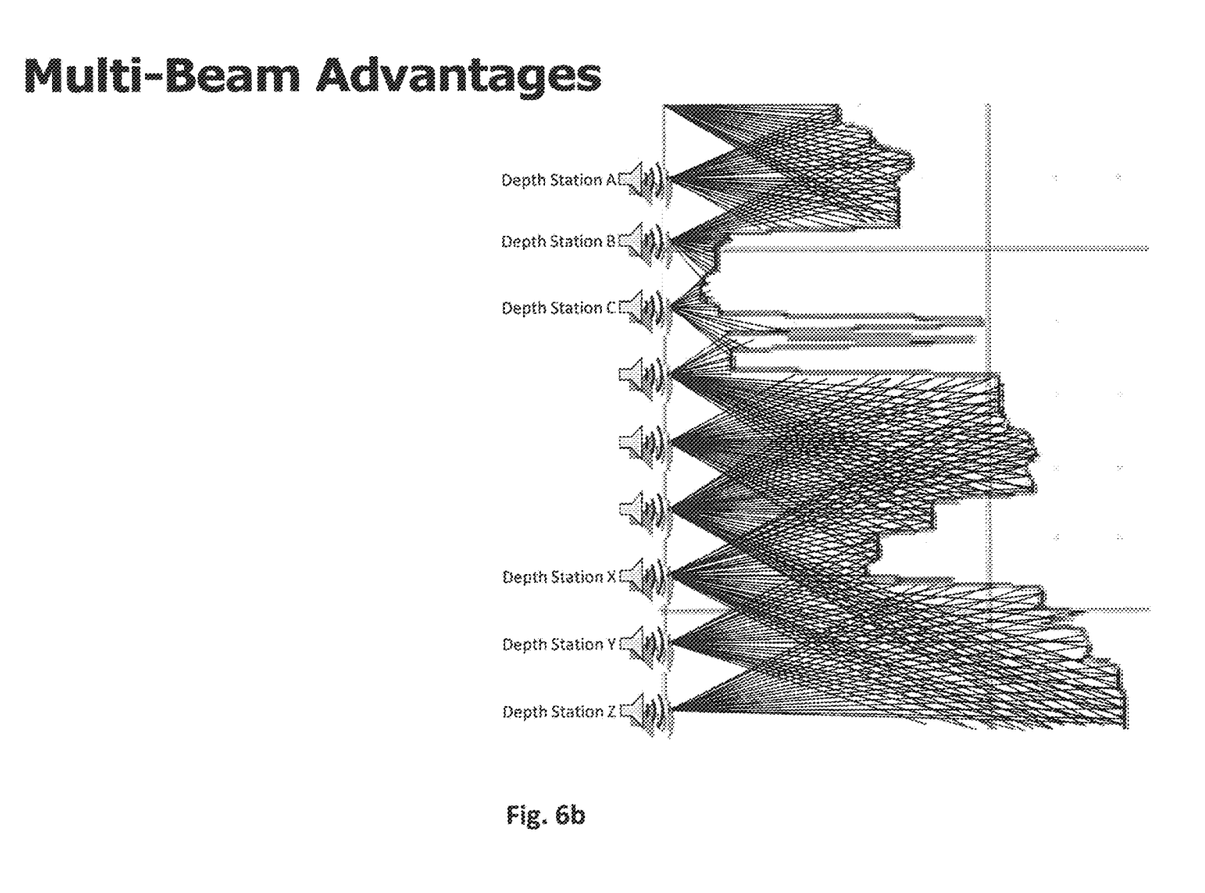
FIG. 6B is a cross sectional view of an exemplary cavern logging survey.
Figure 7:
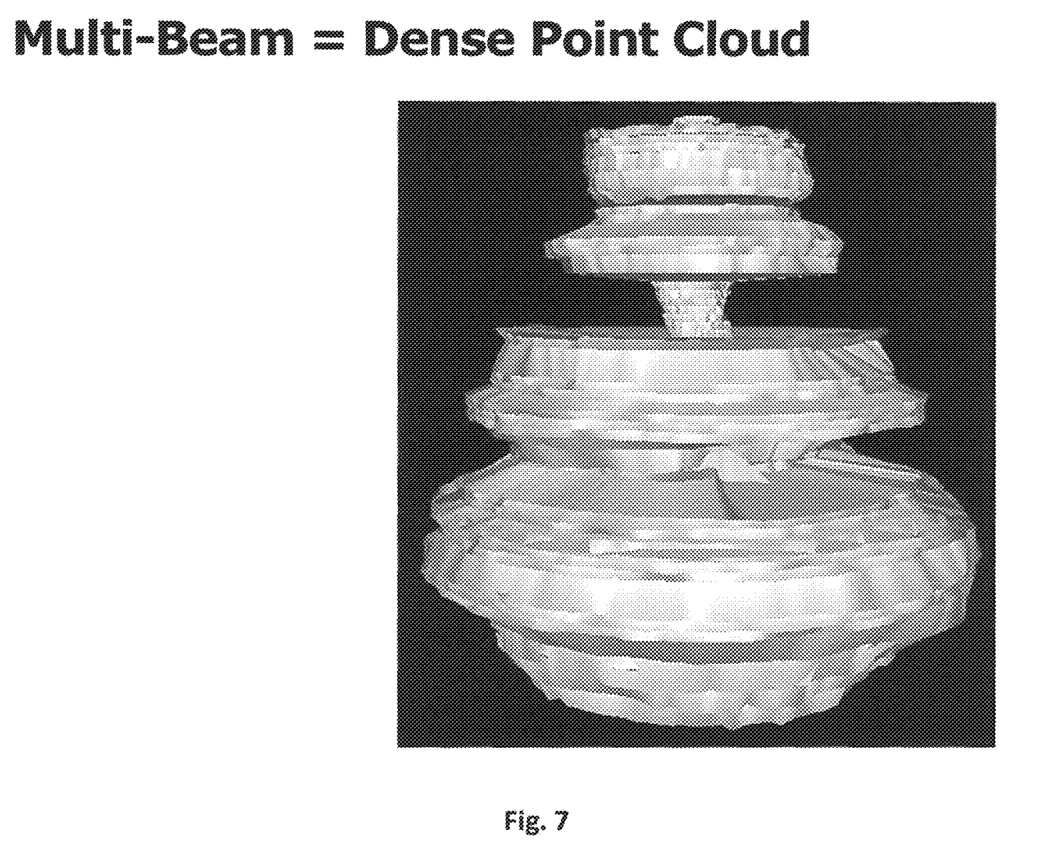
FIG. 7 is a representation of an exemplary cavern logging survey.

The pan and tilt assembly 120 allows the probe transducer 130 to rotate 360° and tilt. This allows the cavern probe 110 to collect a larger amount of data at fewer depth stations within the cavern. Referring to FIG. 6, the pan and tilt assembly 120 may position the cavern probe 110 in the following exemplary configurations in order to inspect a cavern: a 1° wide acoustic beam maybe be panned horizontally thru 360° simultaneously covering ±22.5° vertically from the centerline of a single sweep; tilting the array up from the horizontal centerline by 35° allowing the a 1° wide acoustic beam to be panned thru 360° simultaneously covering +12.5° to +57.5° vertically in a single sweep; titling the array up from the horizontal centerline by +47.5° allowing the 1° wide acoustic beam to be panned thru 360° in a single sweep +47.5° to 92.5° vertically. A similar pattern may be used to inspect lower regions of the cavern and/or the cavern floor. FIG. 7 represents the data points that may be obtained from the cavern probe 110.

The telemetry system 200 is any known automated communications process by which data is received and transmitted. The telemetry system 200 is positioned at a location outside a storage cavern 10.

In some embodiments, the cavern probe 110 is further comprised of a velocimeter 140. The velocimeter 140 is a sonar system that continuously measures the acoustic time of flight to a target at a known distance (e.g. to a cavern wall). If a cavern is contains fluid, for example, the velocimeter 140 measures the varying time of flight through the fluid. The data is used to correct the information received by the probe transducer 130 using any known algorithm.

In some embodiments, the cavern transducer 130, pan and tilt assembly 120, and velocimeter 140 are received in an electronic pressure housing 150 that prevents the cavern transducer 130, the pan and tilt assembly 120, and velocimeter 140 from being damaged by hydrostatic pressures and elevated temperatures. In some embodiments, the housing 150 provides safeguard for pressures up to 25,000 psi and temperatures up to 150° C.

In some embodiments, the electronic pressure housing is a closed, tubular vessel having an endcap 151; the endcap 151 seals with an "O-ring" or other similar device. The endcap 151 allows access to the cavern transducer 130, pan and tilt assembly 120, and velocimeter 140 for maintenance and replacement. In some embodiments, the housing 150 is further comprised of an entry cone 160 and a cable head connector 190.

In some embodiments, the cavern surveyor system 100 is further comprised of an umbilical wireline 170 and a wireline depth encoder 180. The wireline debt encoder 180 measures the amount of wireline payed out from a fixed point providing an accurate measure of the depth of the cavern probe 110. The wireline umbilical 170 allows communication between the cavern probe 110 and the telemetry system 200.

In some embodiments, the telemetry system is comprised of a computing device 210 that receives and transmits information to a communications interface 220. The communications interface 220 is comprised of a wireline depth encoder interface 221 and a wireline umbilical interface 222. The wireline umbilical interface 220 operably mates to the wireline umbilical 170 allowing data to be sent and received from the cavern probe 110 to the telemetry system 200. The wireline depth encoder interface 221 operably mates with the wireline depth encoder 180 allowing probe depth data to be sent to the computing device 210.

In some embodiment, the electronic pressure housing 150 further comprises circuits to effect: data telemetry and tool control communication between the cavern probe (110) and the computing device (210) via the communications interface (220) and wireline umbilical (170); power delivery through the wireline umbilical (170) required for the various electronics assemblies contained in the pressure and temperature resistant housing (150); at least one microprocessor that controls the cavern probe (110) and data communication of acoustic returns to the computing device (210); acoustic transmission, acoustic reception and conditioning of signals to/from the probe transducer (130); velocity of sound measurement of ambient fluid in which the probe transducer (130) is immersed for the purpose of correcting the acoustic data captured by the probe transducer (130); at least one gyro (155) to orient the probe transducer (130) for the purpose of accurately determining the position(s) from which acoustic data is captured; at least one motor that actively positions the probe transducer (130); other sensors (temperature, pressure, etc.) that might be of interest.

What is claimed is:

1. An apparatus to test the integrity of a storage cavern comprising an at least one cavern probe that communicates with a telemetry system; wherein the cavern probe includes an acoustic transducer array comprised of a plurality of transducer elements; wherein the plurality of transducer elements are aligned for directional signal transmission for beamforming and/or spatial filtering of signals; wherein at least one acoustic transducer array transmits signal data to the telemetry system; and a pan and tilt assembly wherein the pan and tilt assembly allow the at least one probe acoustic transducer array to rotate 360° and tilt at least ±90° from a horizontal position.

2. The apparatus of claim 1 further comprising a velocimeter; wherein the velocimeter continuously measures the acoustic time of flight to a target; wherein the velocimeter transmits signal data to the telemetry system.

3. The apparatus of claim 2 further comprising a wireline umbilical; wherein, telemetry system locates the depth of the at least one cavern probe via the wireline umbilical.

4. The apparatus of claim 3 where the at least one acoustic transducer array, pan and tilt assembly, and velocimeter transmits signal data via the telemetry system to the computing device; wherein the computing device provides a visual display of the signal data.

5. A method to use the apparatus of claim 3 comprises:
lowering the cavern probe to first depth in a cavern;
transmitting data via the telemetry system to the cavern probe causing the pan and tilt assembly to sweep 360° on a horizontal plane;
transmitting data to the cavern probe via the telemetry cause the pan and tilt assembly to tilt vertically at least ±90° from the horizontal plane;
transmitting signal data to the telemetry system.

6. The method of claim 5 further comprising:
moving the cavern probe to at least a second depth in the cavern
transmitting data via the telemetry system to the cavern probe causing the pan and tilt assembly to sweep 360° on a horizontal plane;
transmitting data via the telemetry system to the cavern probe cause the pan and tilt assembly to tilt vertically at least ±90° from the horizontal plane;
transmitting signal data to the computing device via the telemetry.

* * * * *